United States Patent
Fukuda et al.

(10) Patent No.: US 11,154,657 B2
(45) Date of Patent: Oct. 26, 2021

(54) METHOD OF AND APPARATUS FOR PERFORMING INTRAVENOUS DRIP INJECTION

(71) Applicant: ARKRAY, Inc., Kyoto (JP)

(72) Inventors: Kazuo Fukuda, Kyoto (JP); Tsuyoshi Takasu, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 382 days.

(21) Appl. No.: 16/220,539

(22) Filed: Dec. 14, 2018

(65) Prior Publication Data
US 2019/0184100 A1    Jun. 20, 2019

(30) Foreign Application Priority Data

Dec. 15, 2017 (JP) .............................. JP2017-240889
Dec. 15, 2017 (JP) .............................. JP2017-240890
Dec. 13, 2018 (JP) .............................. JP2018-233263

(51) Int. Cl.
| | |
|---|---|
| *A61M 5/172* | (2006.01) |
| *A61M 5/142* | (2006.01) |
| *A61M 5/14* | (2006.01) |
| *A61B 5/15* | (2006.01) |
| *A61B 5/151* | (2006.01) |

(52) U.S. Cl.
CPC ......... *A61M 5/1723* (2013.01); *A61B 5/1519* (2013.01); *A61B 5/150022* (2013.01);
(Continued)

(58) Field of Classification Search
CPC .............. A61M 5/1723; A61M 5/1411; A61M 2005/1726; A61M 2205/52; A61M 2205/702; A61M 2230/20
See application file for complete search history.

(56) References Cited

U.S. PATENT DOCUMENTS 5,639,787 A * 6/1997 Riordan .............. A61K 9/0019
   514/449
2006/0030822 A1* 2/2006 Hung .................. A61M 5/1411
   604/246
(Continued)

FOREIGN PATENT DOCUMENTS

JP          4124214 B2    7/2008

OTHER PUBLICATIONS

The Riordan IVC Protocol for Adjunctive Cancer Care Intravenous Ascorbate as a Chemotherapeutic and Biological Response Modifying Agent, online <http://www.doctoryourself.com/RiordanIVC.pdf> (2013).

*Primary Examiner* — Nathan R Price
*Assistant Examiner* — Dung T Ulsh
(74) *Attorney, Agent, or Firm* — Morgan, Lewis & Bockius LLP

(57) ABSTRACT

A method of performing an intravenous drip injection includes a first step, a second step, a third step and a fourth step. A first step includes starting dosing an infusion solution containing a predetermined component by the intravenous drip injection to a dosing recipient. A second step includes extracting a body fluid from the dosing recipient being dosed with the infusion solution. A third step includes measuring a concentration of the predetermined component in the extracted body fluid. A fourth step includes varying the concentration of the predetermined component in the infusion solution, corresponding to the concentration of the predetermined component in the body fluid.

16 Claims, 15 Drawing Sheets

(52) U.S. Cl.
CPC ...... *A61B 5/15087* (2013.01); *A61B 5/15109* (2013.01); *A61B 5/15115* (2013.01); *A61B 5/15117* (2013.01); *A61B 5/15128* (2013.01); *A61B 5/15194* (2013.01); *A61B 5/150748* (2013.01); *A61M 5/1411* (2013.01); *A61M 5/14236* (2013.01); *A61B 5/150412* (2013.01); *A61B 5/150503* (2013.01); *A61M 2005/1726* (2013.01); *A61M 2205/3584* (2013.01); *A61M 2205/50* (2013.01); *A61M 2205/52* (2013.01); *A61M 2205/587* (2013.01); *A61M 2205/702* (2013.01); *A61M 2230/20* (2013.01)

(56) References Cited

U.S. PATENT DOCUMENTS

| | | | |
|---|---|---|---|
| 2007/0191702 A1* | 8/2007 | Yodfat | A61B 5/15 600/365 |
| 2008/0125693 A1* | 5/2008 | Gavin | A61M 1/287 604/29 |
| 2008/0228056 A1* | 9/2008 | Blomquist | A61M 5/1723 600/365 |
| 2008/0281290 A1* | 11/2008 | Yodfat | A61B 5/157 604/504 |
| 2009/0124964 A1* | 5/2009 | Leach | A61B 5/0215 604/66 |
| 2009/0292226 A1* | 11/2009 | Feng | A61B 5/4824 600/595 |
| 2010/0087716 A1* | 4/2010 | Nashed | A61B 5/14503 600/309 |
| 2010/0145262 A1* | 6/2010 | Bengtsson | A61B 5/7275 604/66 |
| 2013/0060228 A1* | 3/2013 | Pazart | A61B 5/150221 604/503 |
| 2015/0196708 A1* | 7/2015 | Mason | A61K 9/19 604/66 |
| 2018/0099090 A1* | 4/2018 | Miyamoto | A61M 5/172 |

\* cited by examiner

METHOD OF AND APPARATUS FOR PERFORMING INTRAVENOUS DRIP INJECTION

CROSS-REFERENCE

This application claims priority to Japanese Patent Application No. 2017-240889, filed on Dec. 15, 2017, Japanese Patent Application No. 2017-240890, filed on Dec. 15, 2017, and Japanese Patent Application No. 2018-233263, filed on Dec. 13, 2018, the entire contents of which are incorporated herein by reference.

FIELD

The present disclosure relates to a method of performing an intravenous drip injection and an apparatus for performing the intravenous drip injection.

BACKGROUND

Ascorbic acid (vitamin C) is ingested by a meal, absorbed by a small intestine and distributed throughout organs and tissues in vivo. Biochemically, the ascorbic acid gets involved in synthesis of collagen, the synthesis of carnitine, the synthesis of adrenal cortex hormone, the synthesis of catecholamine, decomposition of lipid peroxide and the decomposition of active oxygen, and performs an important role in vivo. In recent years, the vitamin C having a strong reductive property has been focused in terms of having anticancer activity, increasing immune strength, and exhibiting a beautiful skin effect and a brightening effect, and has been applied to a high-concentration vitamin C drip infusion therapy and other equivalent therapies. For example, a patent document 1 and a non-patent document 1 described below are given as documents related to the high-concentration vitamin C drip infusion therapy.

DOCUMENTS OF PRIOR ART

Patent Document

[Patent Document 1] Japanese Patent No. 4124214

Non-Patent Document

[Non-Patent Document 1] "The Riordan IVC Protocol for Adjunctive Cancer Care Intravenous Ascorbate as a Chemotherapeutic and Biological Response Modifying Agent", [online], February, 2013, [Searched Oct. 16, 2017], Internet <URL: http://www.doctoryourself.com/RiordanIVC.pdf>

It is an object according to one aspect of a technology of the disclosure to control the concentration of the predetermined component in the body fluid to become equal to or larger than a predetermined concentration.

One aspect of a technology of the disclosure is exemplified by a method of performing an intravenous drip injection. The method includes a first step, a second step, a third step and a fourth step. A first step includes starting dosing an infusion solution containing a predetermined component by the intravenous drip injection to a dosing recipient. A second step includes extracting a body fluid from the dosing recipient being dosed with the infusion solution. A third step includes measuring a concentration of the predetermined component in the extracted body fluid. A fourth step includes varying the concentration of the predetermined component in the infusion solution, corresponding to the concentration of the predetermined component in the body fluid.

The technology of the disclosure is capable of controlling the concentration of the predetermined component in the body fluid to become equal to or larger than the predetermined concentration.

DESCRIPTION OF EMBODIMENTS

Figure 1:
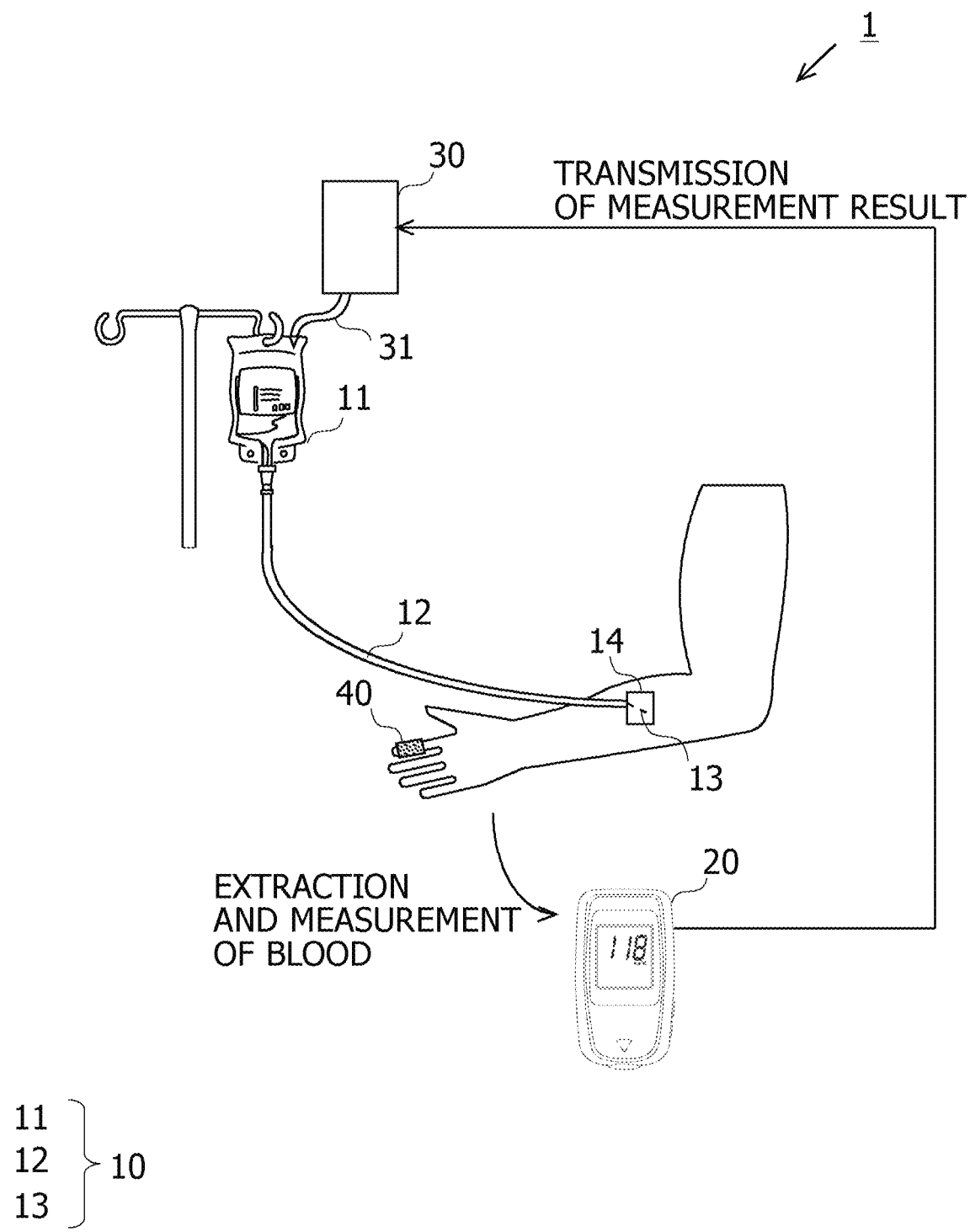
FIG. 1 is a view illustrating one example of a configuration of a drip infusion system according to a first embodiment.

The high-concentration vitamin C drip infusion therapy involves dosing an infusion solution containing ascorbic acid to a patient by an intravenous drip injection. A concentration of the ascorbic acid in a blood extracted from the patient after finishing the intravenous drip injection is measured, and a concentration of the ascorbic acid in the infusion solution to be dosed next time by the high-concentration vitamin C drip infusion therapy is determined based on a measurement result thereof.

After the end of the intravenous drip injection, the concentration of the ascorbic acid in the blood is measured, and hence, during the intravenous drip injection being performed underway, it is unfeasible to determine whether the concentration of the ascorbic acid in the infusion solution being dosed to the patient is proper. It is therefore difficult to control the concentration of the ascorbic acid in the blood to become equal to or larger than a predetermined concentration. Such a problem is, without being limited to the high-concentration vitamin C drip infusion therapy, common to an instance of controlling a concentration, in a body fluid, of a predetermined component to be dosed by the intravenous drip injection.

Embodiments will hereinafter be described. Configurations of the following embodiments are exemplifications, and technologies of the disclosure are not limited to the configurations of the embodiments.

First Embodiment (Method of Performing Intravenous Drip Injection)

A method of performing an intravenous drip injection includes a first step, a second step, a third step and a fourth step. A first step includes starting dosing an infusion solution containing a predetermined component by the intravenous drip injection to a dosing recipient. A second step includes extracting a body fluid from the dosing recipient being dosed with the infusion solution. A third step includes measuring a concentration of the predetermined component in the extracted body fluid. A fourth step includes varying the concentration of the predetermined component in the infusion solution, corresponding to the concentration of the predetermined component in the body fluid.

(First Step)

In the first step, it is started to an infusion solution containing a predetermined component by an intravenous drip injection to a dosing recipient. The intravenous drip injection is performed by, e.g., a drip infusion apparatus. The drip infusion apparatus includes: a drip infusion container that accumulates the infusion solution containing the predetermined component; an injection needle to be detained in vivo; and a tube connecting the container to the injection needle and thereby enabling the infusion solution to flow inside itself. The infusion solution accumulated in the container is dosed in vivo to a patient via the tube and the injection needle.

(Second Step)

In the second step, a body fluid is extracted from the dosing recipient being dosed with the infusion solution. The extraction of the body fluid from the dosing recipient involves using an extraction device. The extraction device, which includes, e.g., a puncture tool, extracts the body fluid by puncturing a body of the dosing recipient with the puncture tool. The extraction device, which is fitted to, e.g., a fingertip of the dosing recipient, may extract the body fluid by puncturing a finger of the dosing recipient. The body fluid is instanced by a blood of the dosing recipient.

(Third Step)

Measured in the third step is a concentration of the predetermined component in the body fluid of the dosing recipient being dosed with the infusion solution containing the predetermined component by the intravenous drip injection. The concentration of the predetermined component is measured by a measuring apparatus to which, e.g., a biosensor is connected. A drop of the body fluid is dispensed to the biosensor, the body fluid being extracted from the dosing recipient being dosed with the infusion solution containing the predetermined component by the intravenous drip injection. When the biosensor, to which the drop of the body fluid is dispensed, is connected to the measuring apparatus, the measuring apparatus measures the concentration of the predetermined component in the body fluid. The predetermined component is instanced by the ascorbic acid.

(Fourth Step)

In a fourth step, a concentration of the predetermined component in the infusion solution is varied corresponding to the concentration of the predetermined component in the body fluid, which is measured in the third step.

For example, an injector, in which the predetermined component is accumulated, is connected to a drip infusion container. In the fourth step, the measured concentration is less than, e.g., a predetermined concentration, in which case the injector injects the predetermined component into a drip infusion container, thereby increasing the concentration of the predetermined component in the infusion solution. A quantity of the predetermined component per time by the injector into the drip infusion container may be restricted to a predetermined quantity. Such a configuration enables the concentration of the predetermined component in the infusion solution to be restrained from being abruptly varied. For example, the quantity of the predetermined component to be added into the infusion solution may also be determined based on a calibration curve plotted to associate a difference between a target concentration of the predetermined component in the body fluid of the dosing recipient and the concentration of the predetermined component in the body fluid of the dosing recipient with the quantity of the predetermined component to be added into the infusion solution, and based on the measured concentration of the predetermined component in the body fluid. Such a configuration enables the concentration of the predetermined component in the blood of the patient to promptly become a predetermined concentration.

(Injector)

The injector includes an accumulation unit, a connecting unit and an injection unit. The accumulation unit is configured to accumulate the predetermined component. The connecting unit is configured to connect the accumulation unit to a drip infusion container to contain the accumulated infusion solution to get the predetermined component flowable therethrough. The injection unit is configured to inject the predetermined component accumulated in the accumulation unit into the drip infusion container via the connecting unit by reducing a capacity of the accumulation unit, corresponding to the concentration of the predetermined component in the body fluid.

The predetermined component is accumulated in the accumulation unit. The accumulation unit may also receive an accumulated drug solution containing the predetermined component having a higher concentration than the concentration of the predetermined component in the infusion solution to be accumulated in the drip infusion container. The accumulation unit and the drip infusion container are connected together by the connecting unit to get the predetermined component flowable therethrough. The connecting unit is instanced by a tube. The injection unit injects the predetermined component accumulated in the accumulation unit into the drip infusion container via the connecting unit by reducing a capacity of the accumulation unit. The accumulation unit is instanced by a syringe. The injection unit may include a plunger sliding within the syringe and may also reduce the capacity of the accumulation unit by actuating the plunger. The accumulation unit is a container configured to have flexibility, and the injection unit may also be configured to reduce the capacity of the accumulation unit by compressing the accumulation unit. The capacity of the accumulation unit is reduced, whereby the accumulated predetermined component is injected into the drip infusion container via the connecting unit. A quantity of the predetermined component to be injected is controllable depending on how much the capacity of the accumulation unit is reduced.

(Control Device)

The method of performing the intravenous drip injection according to the first embodiment is also feasible by a control apparatus exemplified by a computer. The control apparatus is an information processing apparatus including, e.g., a Central Processing Unit (CPU) and a memory. The CPU is also called a Micro Processor Unit (MPU) and a processor. It does not mean that the CPU is limited to the single processor, and the CPU may take a multiprocessor configuration. The memory is exemplified as a storage unit receiving a direct access from the CPU. The memory includes a Random Access Memory (RAM) and a Read Only Memory (ROM). The CPU runs a program stored in the memory, and the control apparatus is thereby enabled to attain the method of performing the intravenous drip injection according to the first embodiment. An apparatus mounted with the control apparatus to attain the method of performing the intravenous drip injection according to the first embodiment, may be said to be an apparatus for performing the intravenous drip injection.

An in-depth description of the method of performing the intravenous drip injection according to the first embodiment described above will hereinafter be made with reference to the accompanying drawings. The following discussion will deal with a high-concentration vitamin C drip infusion therapy (High Dose Vitamin C Therapy), i.e., a case of dosing the ascorbic acid to the patient by the intravenous drip injection. The patient is one example of the "dosing recipient".

FIG. 1 is a view illustrating one example of a configuration of a drip infusion system 1 according to the first embodiment. The drip infusion system 1 includes a drip infusion apparatus 10, a measuring apparatus 20, a supplement apparatus 30, and an extraction device 40.

The drip infusion apparatus 10 includes a drip infusion container 11, a tube 12 and an injection needle 13. The drip infusion container 11 is a container that accumulates the infusion solution. The infusion solution contains the ascorbic acid. The injection needle 13 is detained within a vein of the patient. A medical tape 14 is pasted to a region in which the injection needle 13 is detained, thus restraining the injection needle 13 from coming off. The tube 12 is formed in a hollowed shape. The tube 12 is connected to a bottom portion of the drip infusion container 11 and to the injection needle 13. The tube 12 is connected to the drip infusion container 11, whereby the infusion solution accumulated in the drip infusion container 11 is dosed in vivo to the patient via the tube 12 and the injection needle 13. The drip infusion apparatus 10 is one example of a "drip infusion unit". The supplement apparatus 30 is connected to the drip infusion container 11 via the hollowed tube 12. The supplement apparatus 30 supplements the ascorbic acid to the infusion solution in the drip infusion container 11 via a tube 31. The tube 31 is one example of the "connecting unit".

The measuring apparatus 20 measures a concentration of the ascorbic acid in the blood extracted from the patient. The extraction of the blood involves using the extraction device 40 fitted to, e.g., the fingertip of the patient. The extraction device 40 includes a puncture tool puncturing the fingertip of the patient, and thereby extracts the blood. The measuring apparatus 20 includes, e.g., a biosensor capable of measuring the concentration of the ascorbic acid. The measuring apparatus 20 is connected to the supplement apparatus 30 via an RS-232C cable, and transmits a measurement result to the supplement apparatus 30 via the RS-232C cable. However, a measurement result transmitting method, without being limited to the method via the RS-232C cable, may take wireless communication and may also take wired communications. The measuring apparatus 20 is one example of a "measuring unit". The extraction device 40 is one example of an "extraction unit".

Figure 2:
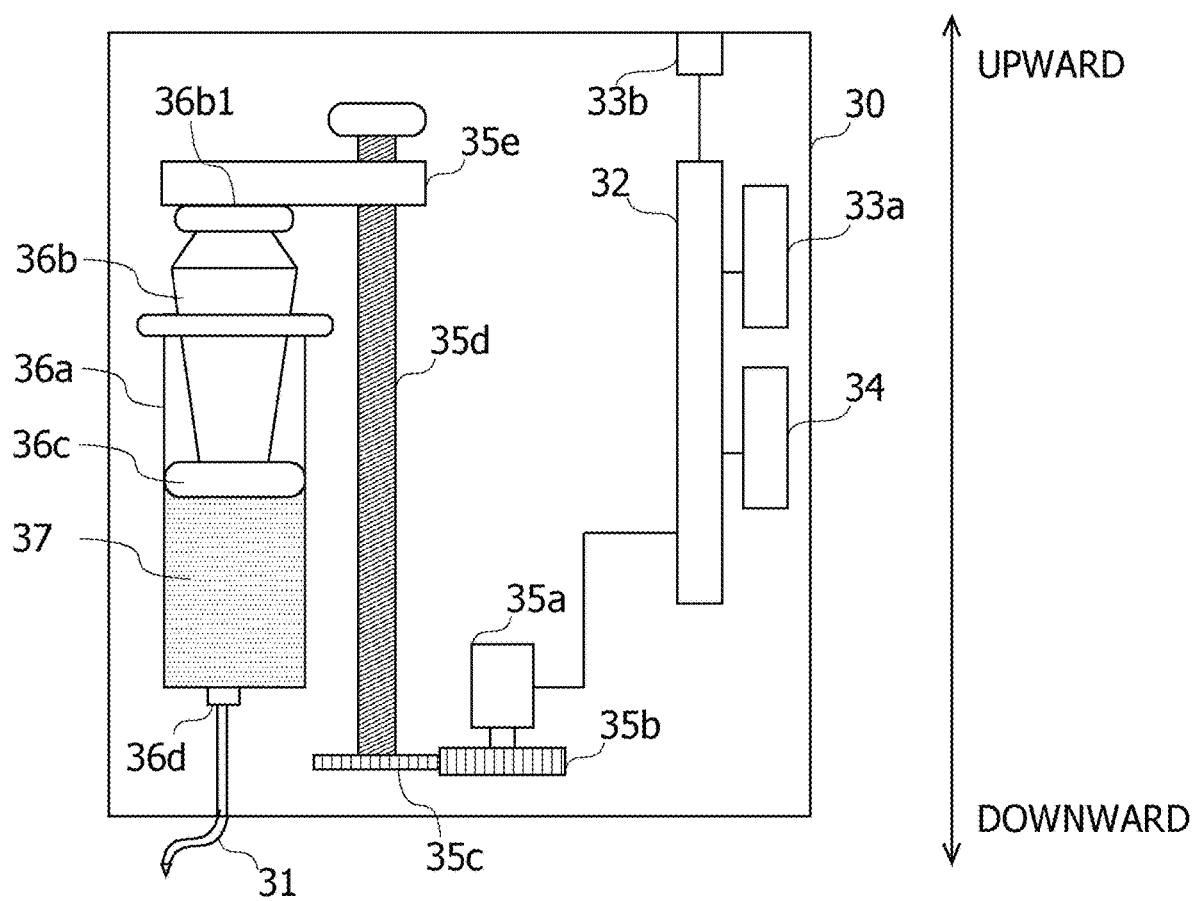
FIG. 2 is a view illustrating one example of a configuration of a supplement apparatus.

The supplement apparatus 30 accumulates the drug solution containing the ascorbic acid having a higher concentration than that of the infusion solution in the drip infusion container 11, and injects the drug solution into the drip infusion container 11, corresponding to the concentration measured by the measuring apparatus 20. FIG. 2 is a view illustrating one example of a configuration of the supplement apparatus 30. In FIG. 2, an upper side is assumed to be a side of an upper edge portion 36$b$1 of a plunger 36$b$ of the injector 36, while a lower side is assumed to be a side of a connecting port 36$d$ of the injector 36. One example of the configuration of the supplement apparatus 30 will hereinafter be described with reference to FIG. 2. The supplement apparatus 30 is one example of a "varying unit".

The supplement apparatus 30 includes a control board 32, a wireless communication module 33$a$, an RS-232C module 33$b$, a display 34, a compression device 35, and the injector 36.

The wireless communication module 33$a$ is a module that performs communications with an external apparatus through wireless communications. The RS-232C module 33$b$ includes a connection terminal to which a communication cable pursuant to standards of the RS-232C is connected. A connection cable extending from the measuring apparatus 20 is connected to the connection terminal of the RS-232C module 33$b$. The RS-232C module 33$b$ is the module performing the communications with the external apparatus via the communication cable connected to the connection terminal and pursuant to the RS-232C standards.

The display 34 displays various items of information, i.e., the concentration of the ascorbic acid in the infusion solution being currently dosed, the measurement result received from the measuring apparatus 20, an elapse time since starting the intravenous drip injection, and other equivalent items.

The control board 32 is enabled to perform the communications with the external apparatus via the wireless communication module 33$a$ and the RS-232C module 33$b$. The control board 32 has the CPU and the memory. The CPU runs the program stored in the memory, whereby the control board 32 implements desired processes.

The injector 36 includes a syringe 36$a$, the plunger 36$b$, a gasket 36$c$, and the connecting port 36$d$. The syringe 36$a$ is formed in a cylindrical shape with an upper edge being opened. Accumulated within the syringe 36$a$ is a drug solution 37 containing the ascorbic acid having the higher concentration than that of the infusion solution accumulated in the drip infusion container 11 of the drip infusion apparatus 10. A bottom portion of the syringe 36$a$ is provided with the connecting port 36$d$ allowing communications between an interior and an exterior of the syringe 36$a$, and the tube 12 is connected to the connecting port 36$d$. The plunger 36$b$ is a rod-shaped member having the gasket 36$c$ at its tip portion. The plunger 36$b$ is inserted from the opening of the upper edge of the syringe 36$a$ so that the gasket 36$c$ side is directed toward the drug solution 37. The upper edge portion 36$b$1 of the plunger 36$b$ contacts a lower surface of an arm portion 35$e$ of the compression device 35. The gasket 36$c$ is formed without any gap between an inner surface of the syringe 36$a$ and this gasket 36$c$. In the injector 36, when the upper edge portion 36b1 of the plunger 36b is compressed toward the connecting port 36d, the plunger 36b moves downward along the inner surface of the syringe 36a. The downward movement of the plunger 36b causes a reduction of the capacity of the syringe 36a. The reduction of the capacity of the syringe 36a causes the drug solution 37 in the syringe 36a to be injected into the drip infusion container 11 of the drip infusion apparatus 10 via the connecting port 36d and the tube 31. The syringe 36a is one example of the "accumulation unit". The tube 31 is one example of the "connecting unit". The compression device 35 and the plunger 36b are one example of an "injection unit".

The compression device 35 is a device that compresses downward the upper edge portion 36b1 of the plunger 36b. The compression device 35 includes a stepping motor 35a, a gear 35b, a gear 35c, a screw shaft 35d and the arm portion 35e. The stepping motor 35a is a motor that rotates by a predetermined quantity per time upon an instruction given from the CPU of the control board 32. A rotary shaft of the stepping motor 35a is provided with the gear 35b engaging with the gear 35c. The screw shaft 35d defined as a rod-shaped member and having screw threads on its outer periphery is formed extending upward from the gear 35c. The arm portion 35e is a plate-shaped member having a screw hole in which the screw shaft 35d is screwed, and is disposed in a way that contacts from upward the upper edge portion 36b1 of the plunger 36b of the injector 36. In the compression device 35, driving force generated by rotations of the stepping motor 35a is transferred to the gear 35c from the gear 35b. The screw shaft 35d is rotated by the driving force transferred through the gear 35c. When the screw shaft 35d is rotated, the arm portion 35e engaging with the screw shaft 35d moves downward. The plunger 36b of the injector 36 is compressed by the arm portion 35e moving downward and is thereby moved downward. The stepping motor 35a rotates by the predetermined quantity, and hence the plunger moves downward by the predetermined quantity. The plunger 36b of the injector 36 descends by the predetermined quantity, whereby the capacity of the syringe 36a decreases by the predetermined quantity. The capacity of the syringe 36a decreases by the predetermined quantity, whereby the predetermined quantity of drug solution 37 is injected into the drip infusion container 11 via the tube 31. The compression device 35 and the plunger 36b are one example of the "injection unit".

<Configuration of Processing Blocks>

Figure 3:
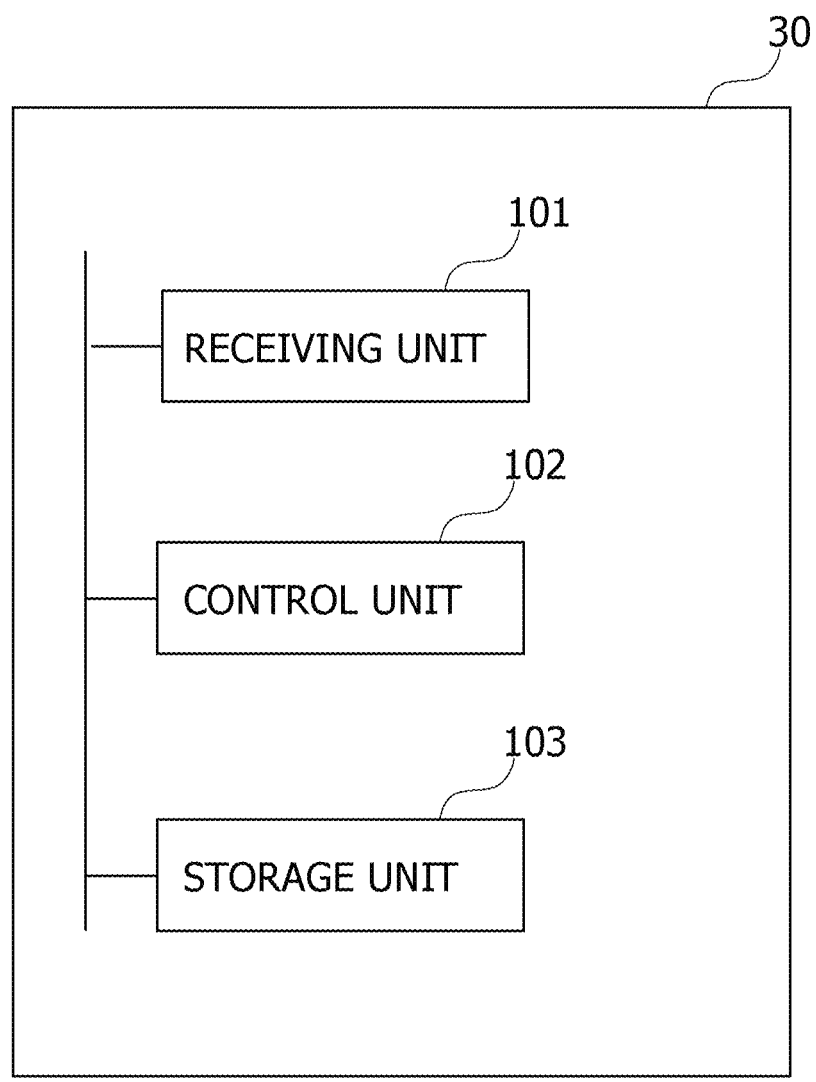
FIG. 3 is a diagram illustrating one example of processing blocks of the drip infusion system according to the first embodiment.

FIG. 3 is a diagram illustrating one example of processing blocks of the drip infusion system 1 according to the first embodiment. The CPU of the control board 32 runs the program stored in the memory, thereby attaining the respective processing blocks illustrated in FIG. 3. However, at least a part of the processing blocks illustrated in FIG. 3 may include hardware circuits. The processing blocks of the drip infusion system 1 according to the first embodiment will hereinafter be described with reference to FIG. 3.

A storage unit 103 stores a setting concentration of the ascorbic acid in the blood of the patient. The setting concentration is a value defined as a target value of the concentration of the ascorbic acid in the blood of the patient with respect to the high-concentration vitamin C drip infusion therapy according to the first embodiment. The storage unit 103 stores the setting concentration in, e.g., an auxiliary storage device of the control board 32. The setting concentration is one example of a "target concentration".

A receiving unit 101 receives the result of the measurement made by the measuring apparatus 20 via the wireless communication module 33a or the RS-232C module 33b. The receiving unit 101 hands over the received measurement result to a control unit 102.

The control unit 102 receives the measurement result given by the measuring apparatus 20 from the receiving unit 101. The control unit 102 determines, based on the setting concentration stored in the storage unit 103 and the measurement result received from the receiving unit 101, whether the concentration of the ascorbic acid in the blood of the patient reaches the setting concentration. When the concentration of the ascorbic acid in the blood does not yet reach the setting concentration, the control unit 102 actuates the compression device 35 to thereby inject the drug solution 37 accumulated in the injector 36 into the drip infusion container 11 of the drip infusion apparatus 10. As described above, the rotation quantity of the stepping motor 35a is regulated to the predetermined quantity, and hence the concentration of the ascorbic acid per injection becomes fixed.

Figure 4:
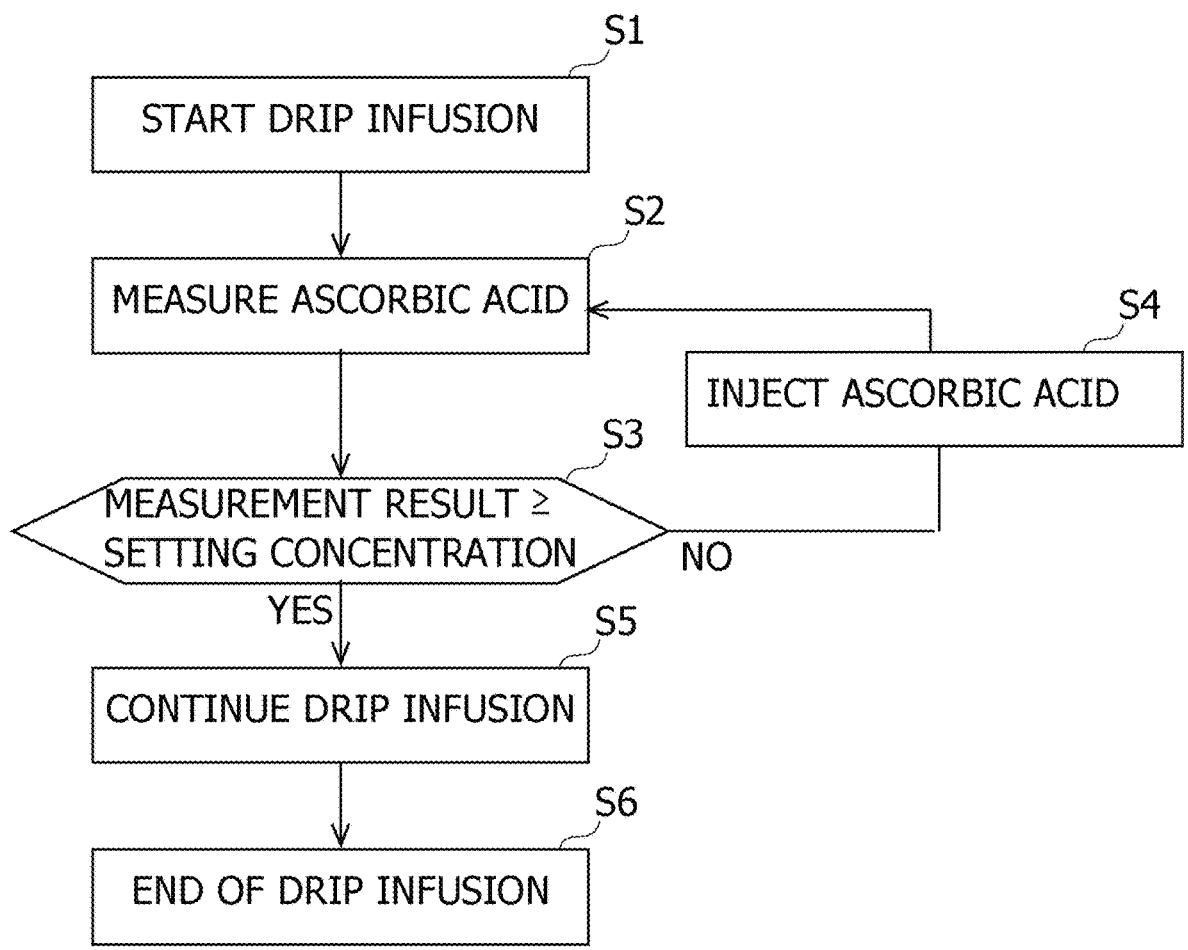
FIG. 4 is a flowchart illustrating one example of a processing flow of the drip infusion system according to the first embodiment.

FIG. 4 is a flowchart illustrating one example of a processing flow of the drip infusion system 1 according to the first embodiment. One example of the processing flow of the drip infusion system 1 according to the first embodiment will hereinafter be described with reference to FIG. 4.

The intravenous drip injection is started in S1. Step S1 is one example of a "first step". In S2, the control unit 102 prompts the measurement of the concentration of the ascorbic acid in the blood of the patient by outputting a message or an alarm at, e.g., every predetermined time. The measuring apparatus 20 measures the concentration of the ascorbic acid in the blood of the patient. With respect to a human body, it is approximately one minute for the blood to flow back to a heart since outflowing in pulsation from the heart. Such being the case, for example, the control unit 102 may prompt the measurement at an interval of one minute or longer. For example, the control unit 102 may also prompt the measurement at a frequency of once per 20 min, 10 min, 5 min or 1 min. The measuring apparatus 20 measures the concentration of the ascorbic acid in the blood extracted from the patient, and transmits the measurement result to the supplement apparatus 30. The receiving unit 101 receives the measurement result transmitted from the measuring apparatus 20. Step S2 is one example of a "second step" and a "third step".

In S3, the control unit 102 determines, based on the setting concentration stored in the storage unit 103 and the measurement result received from the receiving unit 101, whether the concentration of the ascorbic acid in the blood of the patient reaches the setting concentration. When not reaching the setting concentration (No in S3), the processing diverts to S4. Whereas when reaching the setting concentration (Yes in S3), the processing proceeds to S5.

In S4, the control unit 102 actuates the compression device 35 to thereby inject the predetermined quantity of drug solution 37 into the drip infusion container 11 of the drip infusion apparatus 10. As described above, the drug solution 37 contains the ascorbic acid having the higher concentration than that of the infusion solution accumulated in the drip infusion container 11, and therefore this injection enables an increase in concentration of the ascorbic acid of the infusion solution accumulated in the drip infusion container 11. Thereafter, the processing loops back to S2. Step S4 is one example of a "fourth step".

In S5, the concentration of the ascorbic acid in the blood of the patient reaches the setting concentration, and accordingly the intravenous drip injection continues as it is. In S6, when a specified quantity of infusion solution is dozed to the patient, the intravenous drip injection is finished.

Note that the concentration of the ascorbic acid in the blood of the patient is considered unstable immediately after starting the intravenous drip injection. Therefore, for example, the control unit 102 may also set the processes from S2 onward to be executed after an elapse of fixed period of time (e.g., 30 min) since starting the intravenous drip injection.

<Effect of First Embodiment>

In the first embodiment, the blood is extracted from the patient undergoing the intravenous drip injection, and the concentration of the ascorbic acid in the blood is measured. When the concentration, indicated by the measurement result, of the ascorbic acid in the blood does not yet reach the setting concentration, the control unit 102 gets the drug solution 37 to be injected into the drip infusion container 11 of the drip infusion apparatus 10, thereby increasing the concentration of the ascorbic acid in the infusion solution. According to the first embodiment, it is therefore feasible to preferably control the concentration of the ascorbic acid in the infusion solution dosed for the intravenous drip injection being performed underway. As a result, according to the first embodiment, it is possible to control the concentration of the ascorbic acid in the blood of the patient to be equal to or higher than the setting concentration.

In the first embodiment, on the occasion of the injection, the drug solution 37 is injected by the predetermined quantity per time into the drip infusion container 11. According to the first embodiment, it is therefore feasible to restrain the concentration of the ascorbic acid in the infusion solution from being abruptly varied.

<Modified Example of First Embodiment>

In the first embodiment, when the measured concentration of the ascorbic acid in the blood does not yet reach the setting concentration, the predetermined quantity of drug solution 37 is injected into the drip infusion container 11. It does not, however, mean that the quantity of the drug solution 37 injected into the drip infusion container 11 is limited to the predetermined quantity. For example, the control unit 102 sets calibration curve data, compiled to associate a difference between the setting concentration and the concentration of the ascorbic acid in the blood with the quantity of the drug solution 37 injected into the drip infusion container 11, to be stored in the storage unit 103, and may determine the quantity of the drug solution 37 injected into the drip infusion container 11 with reference to the calibration curve data. Such a configuration enables the concentration of the ascorbic acid in the blood of the patient to immediately become the setting concentration.

Second Embodiment

In the first embodiment, the blood is extracted from the patient undergoing the intravenous drip injection being performed underway, and the concentration of the ascorbic acid in the blood is measured. A second embodiment will discuss a technology of measuring the concentration of the ascorbic acid in the blood after finishing the intravenous drip injection.

The high-concentration vitamin C drip infusion therapy involves extracting the blood after finishing the intravenous drip injection and measuring the concentration of the ascorbic acid in the extracted blood. The ascorbic acid is immediately decomposed in the blood, and hence the measurement result fluctuates depending on blood extraction timing. These fluctuations of the measurement result are common to such a case that a concentration of a measurement target component in the body fluid fluctuates depending on an elapse of time till extracting the body fluid since finishing the intravenous drip injection without being limited to the high-concentration vitamin C drip infusion therapy. Such being the case, the second embodiment will discuss a technology of extracting the blood from the patient at fixed timing after finishing the intravenous drip injection as exemplified in the first embodiment, and measuring the concentration of the ascorbic acid in the blood.

(Method of Performing Intravenous Drip Injection)

A method of performing an intravenous drip injection according to the second embodiment further includes a fifth step of detecting an end of the intravenous drip injection exemplified in the first embodiment, and, in the second step, the body fluid is extracted from the dosing recipient at fixed timing after detecting the end of the intravenous drip injection.

The method of performing the intravenous drip injection according to the second embodiment involves detecting the end of the intravenous drip injection in the fifth step. The end of the intravenous drip injection is detected by a detection device that detects the end of the intravenous drip injection. A method by which the detection device detects the end of the intravenous drip injection is not particularly limited. For example, the detection device may also detect the end of the intravenous drip injection by detecting that no infusion solution flows within the tube of the drip infusion apparatus. For instance, when the light is transmittable through the tube of the drip infusion apparatus, the detection device emits the light toward the tube, and may determine, based on an intensity of a reflected flux of emitted light, whether the infusion solution flows within the tube. When the infusion solution does not flow within the tube, the detection device is enabled to detect that the intravenous drip injection is ended.

Upon detecting the end of the intravenous drip injection, the body fluid is extracted from the dosing recipient in the second step. The extraction device extracts the body fluid from the dosing recipient at the fixed timing after detecting the end of the intravenous drip injection. The body fluid is, e.g., the blood. The fixed timing may be set immediately after receiving notification, and may also be set after an elapse of fixed time since receiving the notification.

The puncture tool in the second step includes a puncture unit, a holding unit, an inhibition unit and a cancellation unit. The puncture unit is configured to be ejectable in a predetermined direction. The holding unit is configured to hold a puncture target region of the dosing recipient so as to be located in the predetermined direction from the puncture unit. The inhibition unit is configured to inhibit the puncture unit from being ejected. The cancellation unit is configured to cancel the inhibition of the inhibition unit after a fixed period of time since detecting the end of the intravenous drip injection and to thereby get the puncture unit to be ejected toward the puncture target region.

(Puncture Unit)

The puncture unit is ejectable in a predetermined direction. A tip of the puncture unit is formed in, e.g., a needle-like shape. The puncture unit is ejected in such a state that the needle-shaped tip thereof is set in the predetermined direction. Although a mechanism for ejecting the puncture unit is not particularly limited, the puncture unit is ejected by, e.g., elastic force of a resilient member and by repulsive force of a magnet. For example, the puncture unit may also be ejected by a cam mechanism for transforming an operating force of depressing an ejection button provided on the puncture tool into a motion in the predetermined direction.

(Holding Unit)

The holding unit holds a puncture target region of the dosing recipient so as to be positioned in the predetermined direction from the puncture unit. The holding unit holds the puncture target region, thereby enabling the puncture unit ejecting in the predetermined direction to puncture the puncture target region.

(Inhibition Unit)

The inhibition unit inhibits the puncture unit from being ejected. The inhibition unit inhibits the puncture unit from being ejected, thereby restraining the puncture unit from being ejected at timing other than the timing of extracting the body fluid.

(Cancellation Unit)

The cancellation unit cancels the inhibition of the inhibition unit at fixed timing after detecting the end of the intravenous drip injection. The fixed timing may be set immediately after receiving the end of the intravenous drip injection, and may also be set after an elapse of fixed time since detecting the end of the intravenous drip injection. A method of counting the fixed timing may involve using both of an analog timer and a digital timer. The cancellation unit cancels the inhibition of the inhibition unit, whereby the puncture unit is ejected in the predetermined direction. As described above, the puncture target region held by the holding unit is located in the predetermined direction, and the ejected puncture unit is thereby enabled to puncture the puncture target region.

The cancellation unit includes, e.g., a motor that rotates at a fixed angular speed upon detecting the end of the intravenous drip injection, and a cancellation member provided on a rotary shaft of the motor. The cancellation member being moved by the rotations of the motor rotating at the fixed angular speed sets the inhibition unit in motion, thereby cancelling the inhibition of the inhibition unit. Upon cancelling the inhibition of the inhibition unit, the puncture unit extracts the body fluid by puncturing the puncture target region. The motor rotates at the fixed angular speed as triggered by detecting the end of the intravenous drip injection, and therefore a period of time till extracting the body fluid since the end of the intravenous drip injection becomes fixed. In other words, the motor rotating at the fixed angular speed may be said to be one example of the analog timer.

A solenoid actuator moves the inhibition unit, whereby the cancellation unit may cancel the inhibition of the puncture unit. A start of actuation of the solenoid actuator is triggered by detecting the end of the intravenous drip injection. The solenoid actuator actuates immediately when receiving a signal of the start of actuation, and hence, even when adopting the solenoid actuator as the cancellation unit, the time till extracting the body fluid since the end of the intravenous drip injection becomes fixed. In other words, the solenoid actuator actuating immediately when receiving the signal may be said to be one example of the digital timer.

Figure 5:
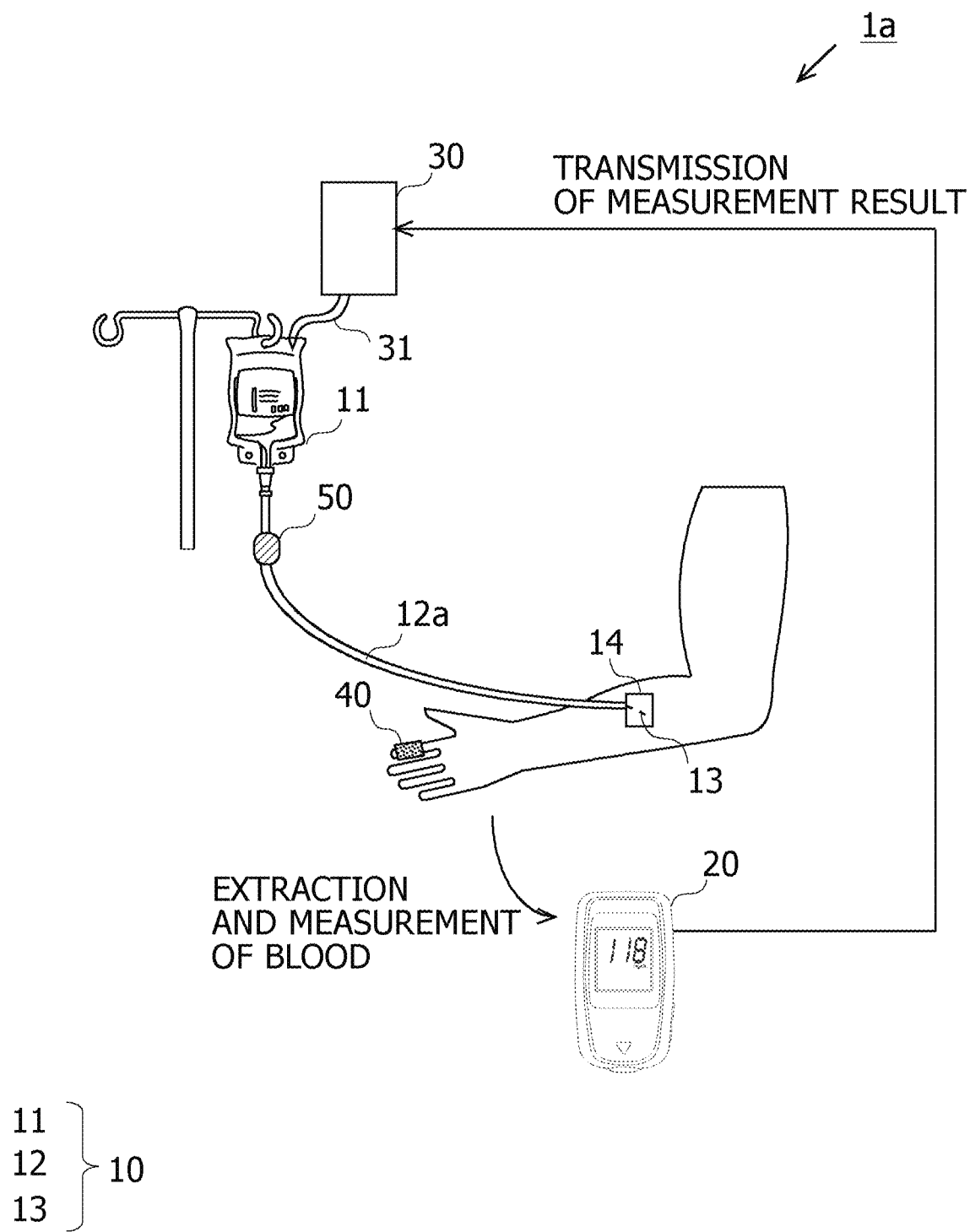
FIG. 5 is a view illustrating one example of a configuration of a drip infusion system according to a second embodiment.

A further in-depth description of the method of performing the intravenous drip injection according to the second embodiment discussed above will hereinafter be made with reference to the following drawings. FIG. 5 is a view illustrating one example of a configuration of a drip infusion system 1*a* according to the second embodiment. The drip infusion system 1*a* is configured by adding a detection device 50 to the configuration of the drip infusion system 1 according to the first embodiment. A tube 12*a* in the second embodiment is composed of a member that allows the transmission of the light.

Figure 6:
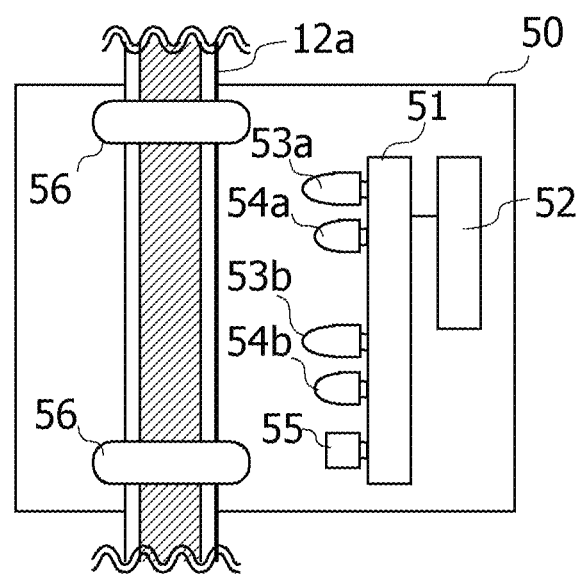
FIG. 6 is a view illustrating one example of a configuration of a detection device.

The detection device 50 is a device to detect the end of the intravenous drip injection. FIG. 6 is a view illustrating one example of a configuration of the detection device 50. The detection device 50 includes a control board 51, a wireless communication module 52, a Light Emitting Diode (LED) 53*a*, an LED 53*b*, a light receiving unit 54*a*, a light receiving unit 54*b*, an alarm 55, and holding members 56, 56.

The holding members 56, 56 hold the tube 12*a* so as not to hinder a flow of the infusion solution within the tube 12*a*. The wireless communication module 52 is a module capable of performing the wireless communications. The control board 51 is communicable with the extraction device 40 via the wireless communication module 52. The control board 51 includes a CPU and a memory. The CPU runs a program stored in the memory, whereby the control board 51 attains desired processes.

The LED 53*a*, the LED 53*b*, the light receiving unit 54*a*, the light receiving unit 54*b* and the alarm 55 are provided on the control board 51. The LED 53*a* and the LED 53*b* are generically termed the LED 53 when not distinguishing therebetween, and the light receiving unit 54*a* and the light receiving unit 54*b* are generically termed the light receiving unit 54 when not distinguishing therebetween. The LED 53 and the light receiving unit 54 are disposed along the tube 12*a*, and a couple of the LED 53*a* and the light receiving unit 54*a* are disposed on a more upstream side of the tube 12*a* than a couple of the LED 53*b* and the light receiving unit 54*b*. Herein, the upstream side of the tube 12*a* is defined as a connecting side of the drip infusion container 11, while a downstream side of the tube 12*a* is defined as a connecting side of the injection needle 13.

The LED 53 is disposed so that an optical axis of the emitted light is directed to the tube 12*a*. The light receiving unit 54 is disposed so that a light receiving surface thereof is directed to the tube 12*a*. When the LED 53 emits the light, at least a part of the emitted light is reflected by the tube 12*a*. The light receiving unit 54*a* is provided in a position in which to receive the reflected beams of light emitted by the LED 53*a*, and the light receiving unit 54*b* is provided in a position in which to receive the reflected beams of light emitted by the LED 53*b*. An intensity of the reflected beams of light reflected by the tube 12*a* differs depending on when the infusion solution flows within the tube 12*a* and when the infusion solution does not flow within the tube 12*a*. The CPU of the control board 51*d* may determine, based on the intensity of the reflected beams of light received by the light receiving unit 54, whether the infusion solution flows within the tube 12*a*.

In the determination, for instance, an intensity range of the intensity of the reflected beams of light when the infusion solution flows within the tube 12*a* may be previously stored in the memory. The CPU of the control board 51 may determine that the infusion solution does not flow within the tube 12*a* when the intensity of the reflected beams of light received by the light receiving unit 54 is beyond the intensity range stored therein. The intensity range of the intensity of the reflected beams of light when the infusion solution does not flow within the tube 12*a* may be stored beforehand in the memory. In this case, the CPU of the control board 51 may determine that the infusion solution does not flow within the tube 12*a* when the intensity of the reflected beams of light received by the light receiving unit 54 is within the intensity range stored therein.

When determining that the infusion solution does not flow within the tube 12a, the CPU of the control board 51 determines that the intravenous drip injection is finished. The CPU of the control board 51 instructs the extraction device 40 to start extracting the blood via the wireless communication module 52 at the fixed timing after detecting the end of the intravenous drip injection. When detecting the end of the intravenous drip injection, the CPU of the control board 51 notifies surroundings of the end of the intravenous drip injection by outputting an alarm sound from the alarm 55.

Figure 7:
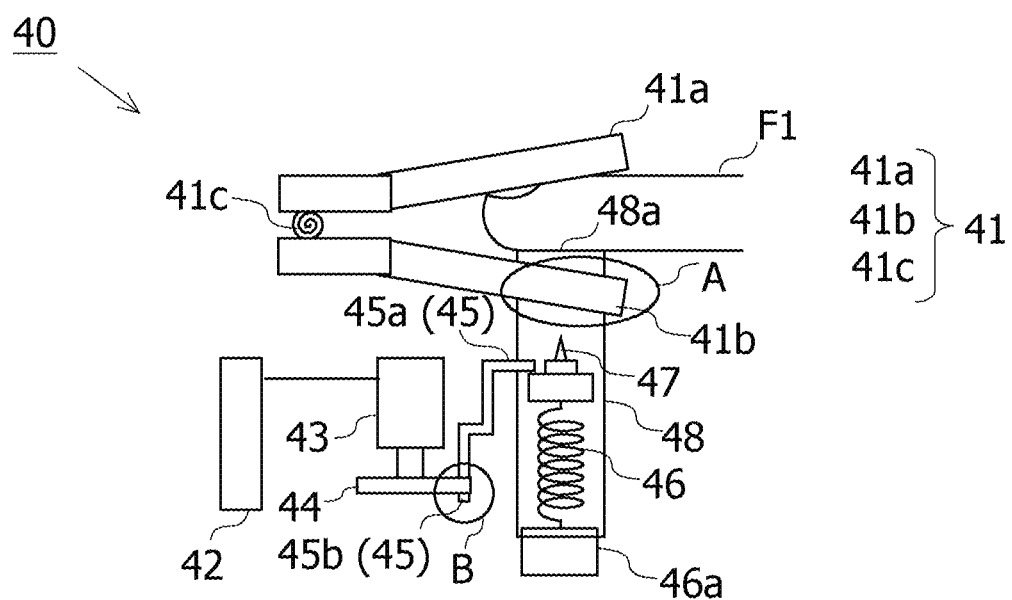
FIG. 7 illustrates one example of a whole schematic view of an extraction device.
Figure 8:
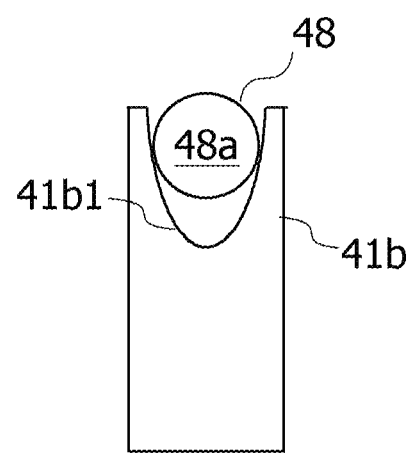
FIG. 8 illustrates one example of a view of a portion encircled by "A" in FIG. 7 as viewed on a plane.
Figure 9:
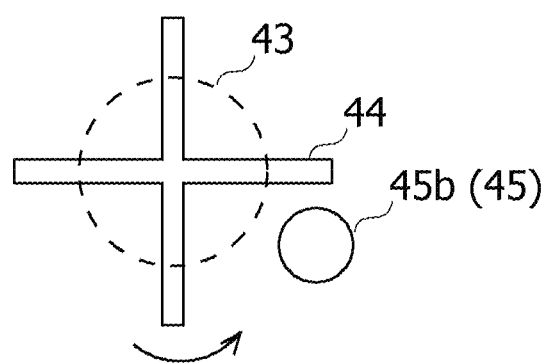
FIG. 9 illustrates one example of a view of a portion encircled by "B" in FIG. 7 as viewed on the plane.

The extraction device 40, as stated above, extracts the blood by puncturing the fingertip of the patient with the puncture tool. FIGS. 7 through 9 are views illustrating one example of a configuration of the extraction device 40. FIG. 7 illustrates one example of a whole schematic view of the extraction device 40. FIG. 8 illustrates one example of a view of a portion encircled by "A" in FIG. 7 as viewed on a plane. FIG. 9 illustrates one example of a view of a portion encircled by "B" in FIG. 7 as viewed on the plane. One example of the configuration of the extraction device 40 will hereinafter be described with reference to FIGS. 7 through 9.

The extraction device 40 includes a clip holding member 41, a motor control unit 42, a stepping motor 43, a stopper cancellation member 44, a stopper member 45, a compression coil spring 46, a base 46a, a puncture member 47 and a housing cylinder 48.

The clip holding member 41 includes a first holding member 41a, a second holding member 41b and a helical torsion coil spring 41c. As understandable by referring to FIG. 8, one end of the second holding member 41b is formed with a recessed portion 41b1 taking a U-shape as viewed on the plane. The second holding member 41b pinches the housing cylinder 48 into the recessed portion 41b1 and is thereby enabled to hold the housing cylinder 48. In the clip holding member 41, elastic force of the helical torsion coil spring 41c is applied to the first holding member 41a and the second holding member 41b in a closing direction. The elastic force of the helical torsion coil spring 41c enables the clip holding member 41 to clip a finger F1 pinched between the first holding member 41a and the second holding member 41b in a state of the finger F1 being pressed against an opening 48a of the housing cylinder 48 held within the recessed portion 41b1. The clip holding member 41 is one example of a "holding unit". The finger F1 is one example of a "puncture target region".

The housing cylinder 48 is a member formed in a cylindrical shape. The base 46a is provided at a bottom portion of the housing cylinder 48. The puncture member 47 and the compression coil spring 46 are provided in an interior of the housing cylinder 48. One end of the compression coil spring 46 is fixed to an upper surface of the base 46a, while the other end is fixed to a bottom surface of the puncture member 47. The opening 48a is provided in an upper portion of the housing cylinder 48. The puncture member 47 is a member having a needle-shaped tip, and extracts the blood by puncturing the finger F1 with the needle. The puncture member 47 is provided on the compression coil spring 46. The stopper member 45 regulates an upward movement of the puncture member 47 by pressing the puncture member 47 from above in a state of an upper edge portion 45a compressing the compression coil spring 46, and a lower edge portion 45b reaches a contact-enabled position with the stopper cancellation member 44. To be specific, the stopper member 45 inhibits the puncture member 47 from being ejected by pressing the puncture member 47 from above in a state of the stopper member 45 being biased by the compression coil spring 46. The stopper member 45 is one example of an "inhibition unit".

The motor control unit 42, upon being instructed by the detection device 50 so as to start extracting the blood, actuates the stepping motor 43. The stepping motor 43 is a motor that rotates, e.g., per ¼ revolution at the fixed angular speed when being instructed by the motor control unit 42. A rotary shaft of the stepping motor 43 is provided with the stopper cancellation member 44.

As depicted in FIG. 9, the stopper cancellation member 44 is rotated by the rotation of the stepping motor 43, and the rotating stopper cancellation member 44 presses the lower edge portion 45b of the stopper member 45. The upper edge portion 45a of the stopper member 45 comes off the puncture member 47 when the lower edge portion 45b is pressed by the stopper cancellation member 44, thereby cancelling the regulation of the stopper member 45 for the ejection of the puncture member 47. When the regulation is cancelled, the puncture member 47 is ejected along the inner surface of the housing cylinder 48 by dint of the elastic force of the compression coil spring 46. The ejected puncture member 47 punctures the finger F1 through the opening 48a of the housing cylinder 48, thus extracting the blood.

A moving range of the puncture member 47 to be ejected is regulated to a range enabling the puncture member 47 to puncture the finger F1 but mitigating a pain felt by the patient with the finger F1 being punctured. The regulation for the moving range of the puncture may be attained by adjusting a length of the compression coil spring 46 and may also be attained by adding a regulation member for regulating the moving range of the puncture member 47 to an upper surface of the housing cylinder 48.

The stepping motor 43 rotates at the fixed angular speed, and hence a period of time till extracting the blood since being instructed by the detection device 50 to start extracting the blood becomes fixed. The extraction device 40 is one example of an "extraction unit". The motor control unit 42, the stepping motor 43 and the stopper cancellation member 44 are one example of a "cancellation unit". The measuring apparatus 20 using, e.g., the biosensor measures the concentration of the ascorbic acid in the blood extracted by the extraction device 40.

<Configuration of Processing Blocks>

Figure 10:
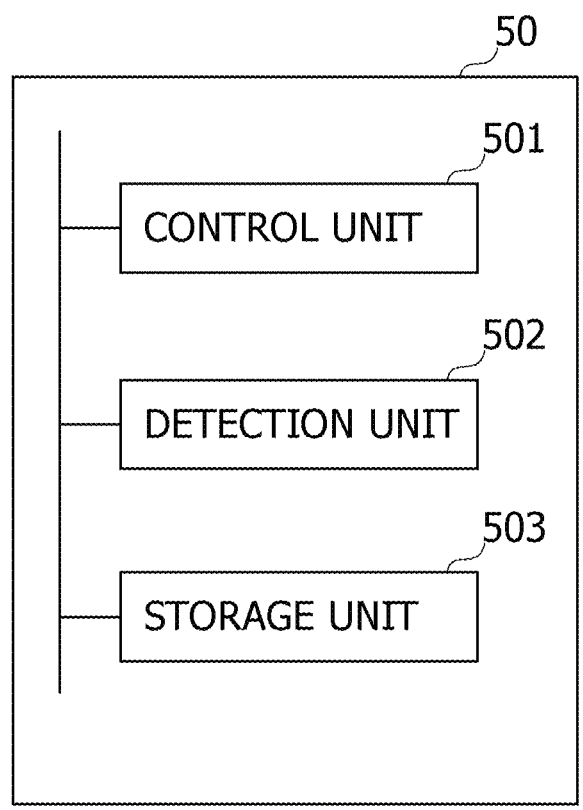
FIG. 10 is a diagram illustrating one example of processing blocks of the detection device according to the second embodiment.

FIG. 10 is a diagram illustrating one example of processing blocks of the detection device 50 according to the second embodiment. The CPU of the control board 51 runs a program stored in the memory, whereby the respective processing blocks illustrated in FIG. 10 are attained. However, at least a part of the processing blocks illustrated in FIG. 10 may include hardware circuits. The processing blocks of the detection device 50 will hereinafter be described with reference to FIG. 10.

A storage unit 503 may store information indicating the intensity range of the intensity of the reflected beams of light when the infusion solution flows within the tube 12a. It may be sufficient that the information to be stored in the storage unit 503 is beforehand determined, e.g., empirically or by other equivalent methods.

The control board 51, when receiving from a detection unit 502 a notification that the intravenous drip injection is finished, causes the alarm 55 to output the alarm sound as well as causing the extraction device 40 to start extracting the blood of the patient.

The detection unit 502 detects the end of the intravenous drip injection. The detection unit 502 may control the LED 53 and the light receiving unit 54. The detection unit 502 causes the LED 53 to emit the light at a predetermined cycle. The detection unit 502 detects the intensity of the light reflected from the tube 12a and received by the light receiving unit 54. The detection unit 502 detects that the intravenous drip injection is finished, based on the detected intensity of the reflected beams of light and on the information stored in the storage unit 503. Herein, the detection unit 502 detects the intravenous drip injection is finished, when an event that the intravenous drip injection is finished is indicated based on such information that both of the intensity of the reflected beams of light received by the light receiving unit 54a and the intensity of the reflected beams of light reflected by the light receiving unit 54b, are stored in the storage unit 503. The detection unit 502, when detecting that the intravenous drip injection is finished, notifies a control unit 501 of this purport. The detection unit 502 is one example of a "detection unit".

Figure 11:
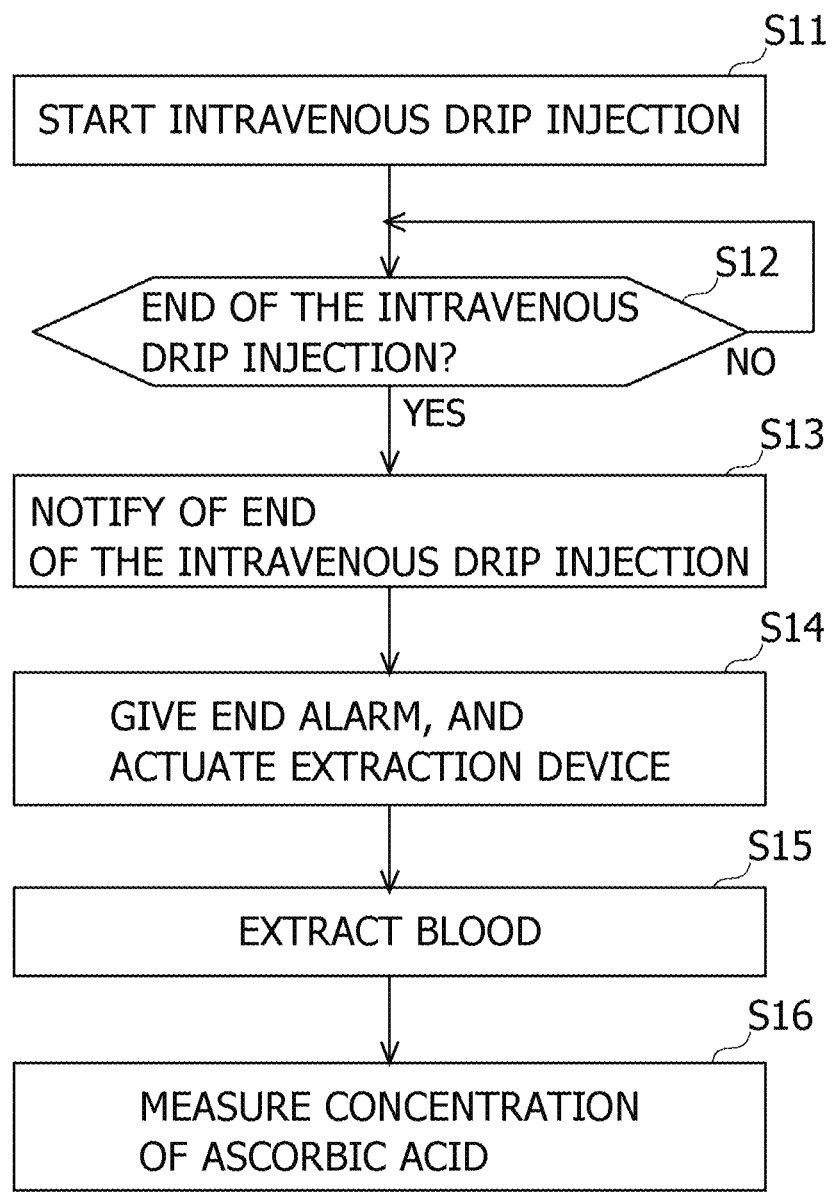
FIG. 11 is a flowchart illustrating one example of a processing flow of the drip infusion system according to the second embodiment.

FIG. 11 is a flowchart illustrating one example of a processing flow of the drip infusion system 1a according to the second embodiment. One example of the processing flow of the drip infusion system 1a according to the second embodiment will hereinafter be described with reference to FIG. 11.

In S11, the intravenous drip injection is started. When starting the intravenous drip injection, as illustrated in FIG. 7, the clip holding member 41 of the extraction device 40 clips the finger F1 of the patient in the state of the finger F1 being pressed against the opening 48a of the housing cylinder 48. The process in S11 is one example of a "first step".

It is determined in S12 whether the intravenous drip injection is finished. The detection unit 502 causes the LED 53 to emit the light, and detects the intensity of the light reflected from the tube 12a and received by the light receiving unit 54. The detection unit 502 determines, based on the detected intensity of the reflected beams of light and the information stored in the storage unit 503, whether the intravenous drip injection is finished. When the intravenous drip injection is finished (YES in S12), the processing proceeds to S13. Whereas when the intravenous drip injection is not finished (NO in S12), the detection unit 502 loops back the processing to S12. The process in S12 is one example of a "fifth step".

In S13, the control unit 501 receives the notification of the end of the intravenous drip injection from the detection unit 502. In S14, the control unit 501 being notified of the end of the intravenous drip injection causes the extraction device 40 to start extracting the blood. The extraction device 40, as described above, punctures the finger F1 of the patient with the puncture member 47 at the fixed timing after detecting the end of the intravenous drip injection. In S15, the blood is extracted from the punctured finger F1 of the patient. The processes in S14 through S15 are one example of a "second step". In S16, the measuring apparatus 20 using, e.g., the biosensor measures the concentration of the ascorbic acid in the blood. The process in S16 is one example of a "third step". The measuring apparatus 20 is one example of a "measuring unit".

<Effect of Second Embodiment>

In the second embodiment, the control unit 501 being notified of the end of the intravenous drip injection from the detection unit 502 instructs the extraction device 40 to start extracting the blood at the fixed timing after receiving the notification. The extraction device 40 instructed by the control unit 501 cancels the regulation of the stopper member 45 through the stopper cancellation member 44 provided on the rotary shaft of the stepping motor 43 rotating at the fixed rotating speed. The puncture member 47 with the regulation being cancelled punctures the finger F1, thus extracting the blood. As a result, a period of time till giving the instruction to start extracting the blood since being notified of the end of the intravenous drip injection is fixed, and a period of time till actually extracting the blood since giving the instruction to start extracting the blood is also fixed. It is therefore feasible to make fixed the time till the blood extraction since the end of the intravenous drip injection.

In the second embodiment, the end of the intravenous drip injection is detected, when the event that the intravenous drip injection is finished is indicated based on such information that both of the intensity of the reflected beams of light detected by the light receiving unit 54a and the intensity of the reflected beams of light detected by the light receiving unit 54b, are stored in the storage unit 503. In the second embodiment, the two light receiving units 54 dually check the end of the intravenous drip injection, whereby such a possibility is restrained that the intravenous drip injection is not actually ended, but nevertheless the end of the intravenous drip injection is mistakenly detected.

<Modified Example of Second Embodiment>

In the second embodiment, the light receiving unit 54a detects the end of the intravenous drip injection by measuring the intensity of the reflected beams of light from the tube 12a. A method of detecting the end of the intravenous drip injection is not, however, limited to this method. For example, the light receiving unit 54 and the LED 53 are disposed in a face-to-face relationship with the tube 12a being interposed therebetween, and the light receiving unit 54 receives transmitted beams of light emitted from the LED 53 and penetrating the tube 12a. The detection unit 502 causes the light receiving unit 54 to detect the intensity of the transmitted beams of light received by the light receiving unit 54, and may simply detect the end of the intravenous drip injection, based on the detected intensity of the transmitted beams of light.

In the second embodiment, the puncture member 47 is ejected by the elastic force of the compression coil spring 46. A means to eject the puncture member 47 is not, however, limited to the compression coil spring 46. As the ejection means, the puncture member 47 may be ejected by the elastic force of the resilient member such as a plate spring or by elastic force of an elastic member such as a rubber. The puncture member 47 and the base 46a are magnetized, with same poles (e.g., the S-pole and the S-pole) facing each other, and the puncture member 47 may also be ejected by repulsive force of the magnet.

Figure 12A:
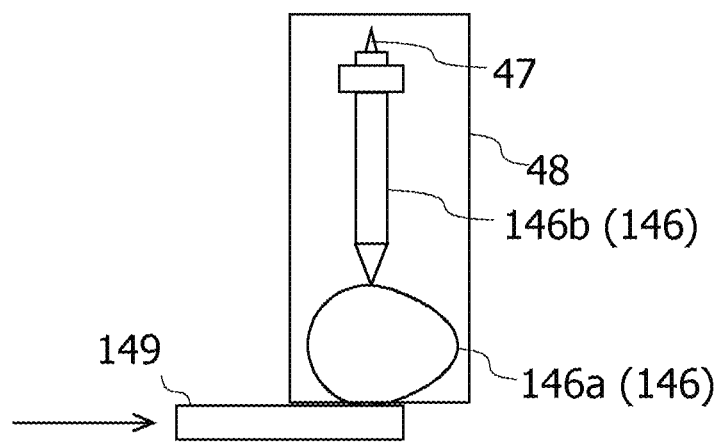
FIG. 12A is a first view illustrating one example of a configuration in which a puncture member is ejected by a cam mechanism.
Figure 12B:
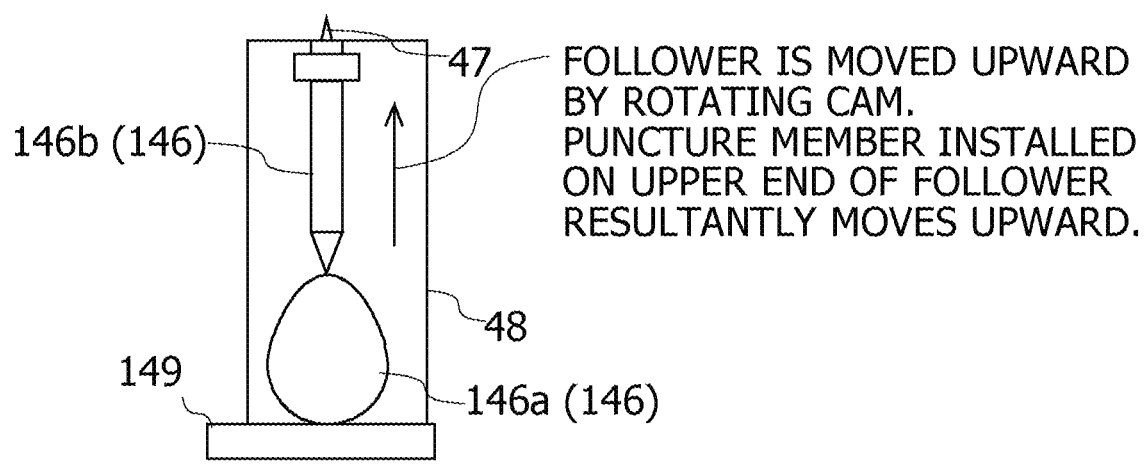
FIG. 12B is a second view illustrating one example of a configuration in which the puncture member is ejected by the cam mechanism.

The puncture member 47 may also be ejected by a cam mechanism in place of the elastic force and the repulsive force. FIGS. 12A and 12B are views each illustrating one example of a configuration of a cam mechanism 146 that ejects the puncture member 47. The cam mechanism 146 includes a cam 146a and a follower 146b. The puncture member 47 is provided on an upper end of the follower 146b, and a lower end thereof is contiguous to the cam 146a. The cam 146a and a button 149 are disposed so as to contact each other. When pressing the button 149 in a state of FIG. 12A, the cam 146a is rotated by dint of frictional force with the button 149. As depicted in FIG. 12B, the follower 146b is moved upward by the rotating cam 146a, thereby enabling the puncture member 47 to be ejected upward.

In the second embodiment, the stopper cancellation member 44 provided on the rotary shaft of the stepping motor 43 rotating at the fixed rotating speed cancels the regulation of the stopper member 45, thereby making fixed the period of time till extracting the blood since being instructed by the detection device 50 to start extracting the blood. A mechanism for making fixed the period of time till extracting the blood since being instructed by the detection device 50 to start extracting the blood is not, however, limited to the mechanism described above. For example, the stopper member may be actuated by the solenoid actuator.

Figure 13A:
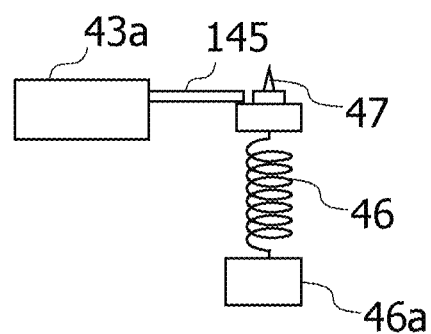
FIG. 13A is a first view illustrating one example of a configuration in which a solenoid actuator actuates a stopper member.
Figure 13B:
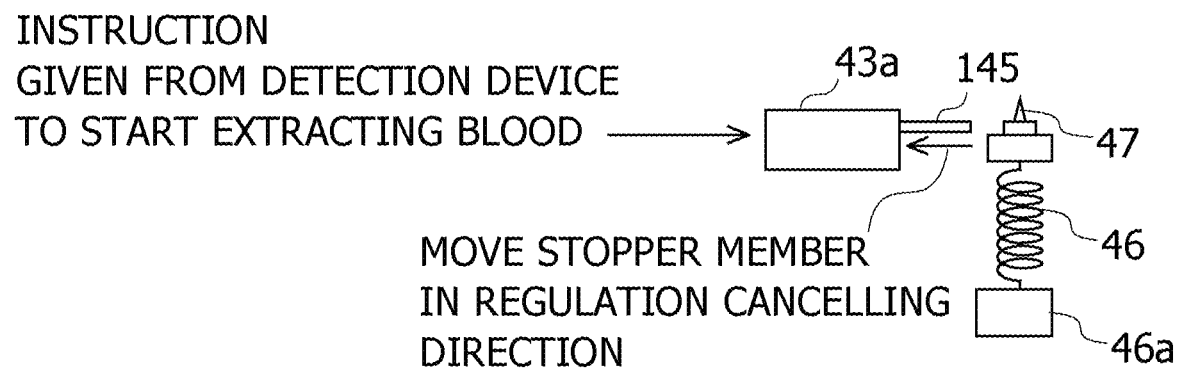
FIG. 13B is a second view illustrating one example of a configuration in which the solenoid actuator actuates the stopper member.

FIGS. 13A and 13B are views each illustrating one example of a configuration of how a solenoid actuator 43a actuates a stopper member 145. During a period till being instructed by the detection device 50 to start extracting the blood, as illustrated in FIG. 13A, the stopper member 145 regulates the upward movement of the puncture member 47 by pressing the puncture member 47 from above. Upon receiving the instruction to start extracting the blood from the detection device 50, the solenoid actuator 43a, as depicted in FIG. 13B, gets the stopper member 145 to move in such a direction as to cancel the regulation. The solenoid actuator 43a operates immediately when receiving the instruction to extract the blood from the detection device 50, and also the mechanism illustrated in FIGS. 13A and 13B is therefore enabled to make fixed the period of time till extracting the blood since being instructed by the detection device 50. Note that when the puncture member 47 is ejected by the cam mechanism 146 as depicted in FIGS. 12A and 12B, the solenoid actuator 43a gets the cam 146a to rotate, and the puncture member 47 may be thereby ejected upward.

The embodiments and the modified examples disclosed above may be combined respectively. For example, the blood may be extracted at the fixed timing in S2 of FIG. 4 by combining the first embodiment with the second embodiment. The blood may also be extracted during the intravenous drip injection being performed underway in such a way that, e.g., the control unit 501 actuates the extraction device 40 at the fixed timing after an elapse of the predetermined time per elapse of the fixed time to thereby puncture the finger F1. The fixed timing may be set immediately after an elapse of the predetermined time, and may also be set after an elapse of the fixed time since the elapse of the predetermined time. The control unit 501 executes these processes and is thereby enabled to make fixed an interval of the blood extraction during the intravenous drip injection being performed underway with higher accuracy than by the first embodiment. As a result, there is restrained the fluctuation of the measurement result of the ascorbic acid decomposed forthwith in the blood.

<<Non-Transitory Computer Readable Recording Medium>>

An information processing program making a computer, other machines and apparatuses (which will hereinafter be referred to as the computer and other equivalent apparatuses) attain any one of the functions, is recordable on a non-transitory recording medium readable by the computer and other equivalent apparatuses. The computer and other equivalent apparatuses are made to read and run the program on this non-transitory recording medium, whereby the function thereof can be provided.

Herein, the non-transitory recording medium readable by the computer and other equivalent apparatuses connotes a non-transitory recording medium capable of accumulating information instanced by data and programs electrically, magnetically, optically, mechanically or by chemical action, which are readable from the computer and other equivalent apparatuses. Among these non-transitory recording mediums, the mediums removable from the computer and other equivalent apparatuses are exemplified by a flexible disc, a magneto-optic disc, a Compact Disc Read Only Memory (CD-ROM), a Compact Disc-Recordable (CD-R), a Compact Disc-ReWriterable (CD-RW), a Digital Versatile Disc (DVD), a Blu-ray disc (BD), a Digital Audio Tape (DAT), an 8 mm tape, and a memory card like a flash memory. A hard disc, the ROM and other equivalent recording mediums are given as the non-transitory recording mediums fixed within the computer and other equivalent apparatuses.

What is claimed is:

1. A method of performing an intravenous drip injection, the method comprising:
   a first step of starting dosing an infusion solution containing a predetermined component by the intravenous drip injection to a dosing recipient;
   a second step of extracting a body fluid from the dosing recipient being dosed with the infusion solution;
   a third step of measuring a concentration of the predetermined component in the extracted body fluid; and
   a fourth step of varying the concentration of the predetermined component in the infusion solution, corresponding to the concentration of the predetermined component in the body fluid,
   wherein a target concentration of the predetermined component in the body fluid of the dosing recipient is specified in the intravenous drip injection, and the fourth step includes adding, into the infusion solution, the predetermined component having a quantity determined based on a calibration curve plotted to associate a difference between the concentration of the predetermined component in the body fluid of the dosing recipient and the target concentration thereof with a quantity of the predetermined component to be added into the infusion solution, and based on the measured concentration of the predetermined component in the body fluid.

2. The method of performing the intravenous drip injection according to claim 1, wherein the fourth step includes adding the predetermined component by a predetermined quantity into the infusion solution.

3. The method of performing the intravenous drip injection according to claim 1, wherein the concentration of the predetermined component is varied in the fourth step by an injector, the injector including: an accumulation unit configured to accumulate the predetermined component; a connecting unit configured to connect the accumulation unit to a drip infusion container to contain the accumulated infusion solution to get the predetermined component flowable therethrough; and an injection unit configured to inject the predetermined component accumulated in the accumulation unit into the drip infusion container via the connecting unit by reducing a capacity of the accumulation unit, corresponding to the concentration of the predetermined component in the body fluid.

4. The method of performing the intravenous drip injection according to claim 1, wherein the first step of starting dosing the infusion solution containing the predetermined component by the intravenous drip injection to the dosing recipient and then detecting an end of the intravenous drip injection, the second step including extracting the body fluid from the dosing recipient at fixed timing after detecting the end of the intravenous drip injection.

5. The method of performing the intravenous drip injection according to claim 4, wherein the second step includes extracting the body fluid by puncturing a body of the dosing recipient with a puncture tool at the fixed timing after detecting the end of the intravenous drip injection.

6. The method of performing the intravenous drip injection according to claim 5, wherein the puncture tool in the second step includes: a puncture unit configured to be ejectable in a predetermined direction; a holding unit configured to hold a puncture target region of the dosing recipient so as to be located in the predetermined direction from the puncture unit; an inhibition unit configured to inhibit the puncture unit from being ejected; and a cancellation unit configured to cancel the inhibition of the inhibition unit after a fixed period of time since detecting the end of the intravenous drip injection and to thereby get the puncture unit to be ejected toward the puncture target region.

7. The method of performing the intravenous drip injection according to claim 1, wherein the predetermined component is ascorbic acid.

8. The method of performing the intravenous drip injection according to claim 1, wherein the body fluid is a blood of the dosing recipient.

9. An apparatus for performing an intravenous drip injection, the apparatus comprising:
   a drip infusion unit to dose an infusion solution containing a predetermined component by the intravenous drip injection to a dosing recipient;
   an extraction unit to extract a body fluid from the dosing recipient being dosed with the infusion solution; a measuring unit to measure a concentration of the predetermined component in the extracted body fluid; and
   a varying unit to vary the concentration of the predetermined component in the infusion solution, corresponding to the concentration of the predetermined component in the body fluid,
   wherein a target concentration of the predetermined component in the body fluid of the dosing recipient is specified in the intravenous drip injection, and the varying unit adds, into the infusion solution, the predetermined component having a quantity determined based on a calibration curve plotted to associate a difference between the concentration of the predetermined component in the body fluid of the dosing recipient and the target concentration thereof with a quantity of the predetermined component to be added into the infusion solution, and based on the measured concentration of the predetermined component in the body fluid.

10. The apparatus for performing the intravenous drip injection according to claim 9, wherein the varying unit adds the predetermined component by a predetermined quantity into the infusion solution.

11. The apparatus for performing the intravenous drip injection according to claim 9, wherein the varying unit includes: an accumulation unit configured to accumulate the predetermined component; a connecting unit configured to connect the accumulation unit to a drip infusion container to contain the accumulated infusion solution to get the predetermined component flowable therethrough; and an injection unit configured to inject the predetermined component accumulated in the accumulation unit into the drip infusion container via the connecting unit by reducing a capacity of the accumulation unit, corresponding to the concentration of the predetermined component in the body fluid.

12. The apparatus for performing the intravenous drip injection according to claim 9, further comprising a detection unit configured to detect an end of the intravenous drip injection for dosing a predetermined component to the dosing recipient, the extraction unit extracting the body fluid from the dosing recipient at fixed timing after detecting the end of the intravenous drip injection.

13. The apparatus for performing the intravenous drip injection according to claim 12, wherein the extraction unit extracts the body fluid by puncturing a body of the dosing recipient with a puncture tool at the fixed timing after detecting the end of the intravenous drip injection.

14. The apparatus for performing the intravenous drip injection according to claim 13, wherein the puncture tool includes: a puncture unit configured to be ejectable in a predetermined direction; a holding unit configured to hold a puncture target region of the dosing recipient so as to be located in the predetermined direction from the puncture unit; an inhibition unit configured to inhibit the puncture unit from being ejected; and a cancellation unit configured to cancel the inhibition of the inhibition unit after a fixed period of time since detecting the end of the intravenous drip injection and to thereby get the puncture unit to be ejected toward the puncture target region.

15. The apparatus for performing the intravenous drip injection according to claim 9, wherein the body fluid is a blood of the dosing recipient.

16. The apparatus for performing the intravenous drip injection according to claim 9, wherein the predetermined component is ascorbic acid.

* * * * *